United States Patent
Jamison

(10) Patent No.: US 12,324,378 B2
(45) Date of Patent: Jun. 10, 2025

(54) TECHNIQUES AND IMPLEMENTATIONS FOR IMPROVED CROP YIELDS IN ARID CONDITIONS

(71) Applicant: John Jamison, Dickerson, MD (US)

(72) Inventor: John Jamison, Dickerson, MD (US)

( * ) Notice: Subject to any disclaimer, the term of this patent is extended or adjusted under 35 U.S.C. 154(b) by 177 days.

(21) Appl. No.: 17/900,012

(22) Filed: Aug. 31, 2022

(65) Prior Publication Data

US 2023/0066873 A1    Mar. 2, 2023

Related U.S. Application Data

(60) Provisional application No. 63/239,440, filed on Sep. 1, 2021.

(51) Int. Cl.
*A01G 22/25* (2018.01)
*A01H 1/00* (2006.01)

(52) U.S. Cl.
CPC .............. *A01G 22/25* (2018.02); *A01H 1/12* (2021.01)

(58) Field of Classification Search
CPC ........... A01G 22/25; A01G 20/00; A01H 1/12
See application file for complete search history.

(56) References Cited

U.S. PATENT DOCUMENTS

| | | | | |
|---|---|---|---|---|
| 5,278,057 A | * | 1/1994 | Jorgensen | C12N 15/65 800/317.4 |
| 5,606,823 A | * | 3/1997 | Souza | A01G 7/00 47/89 |
| 7,939,466 B2 | | 5/2011 | Ricks | |
| 2019/0239421 A1 | | 8/2019 | Fritsch | |
| 2021/0010993 A1 | | 1/2021 | Shibata et al. | |

FOREIGN PATENT DOCUMENTS

| | | | | |
|---|---|---|---|---|
| WO | WO-9211376 A1 | * | 7/1992 | ......... C12N 15/1137 |
| WO | WO-2012112529 A1 | * | 8/2012 | ............. C08B 1/003 |

OTHER PUBLICATIONS

Sweet Potatoes Make a Surprising Cover Crop By Sarah Hill posted on Oct. 1, 2019.*

* cited by examiner

*Primary Examiner* — Ebony E Evans
(74) *Attorney, Agent, or Firm* — Potomac Law Group, PLLC

(57) ABSTRACT

Disclosed implementations for improving crop yield in arid environments. Implementations include a method comprising selecting a cover crop adapted to absorb one or more of atmospheric or soil moisture for storage in an underground portion of the cover crop, and planting the selected cover crop in a particular tract of land at a first time instance. The method additionally includes controllably terminating growth of the cover crop at a second time instance, subsequent to the first time instance, to initiate a decay phase of the cover crop to cause transfer of the moisture absorbed in the underground portion of the cover crop to soil of the tract of land, and planting a primary crop in the tract of land at a third time instance, the primary crop absorbing from the soil at least some of the moisture released during the decay phase of the cover crop.

9 Claims, 1 Drawing Sheet

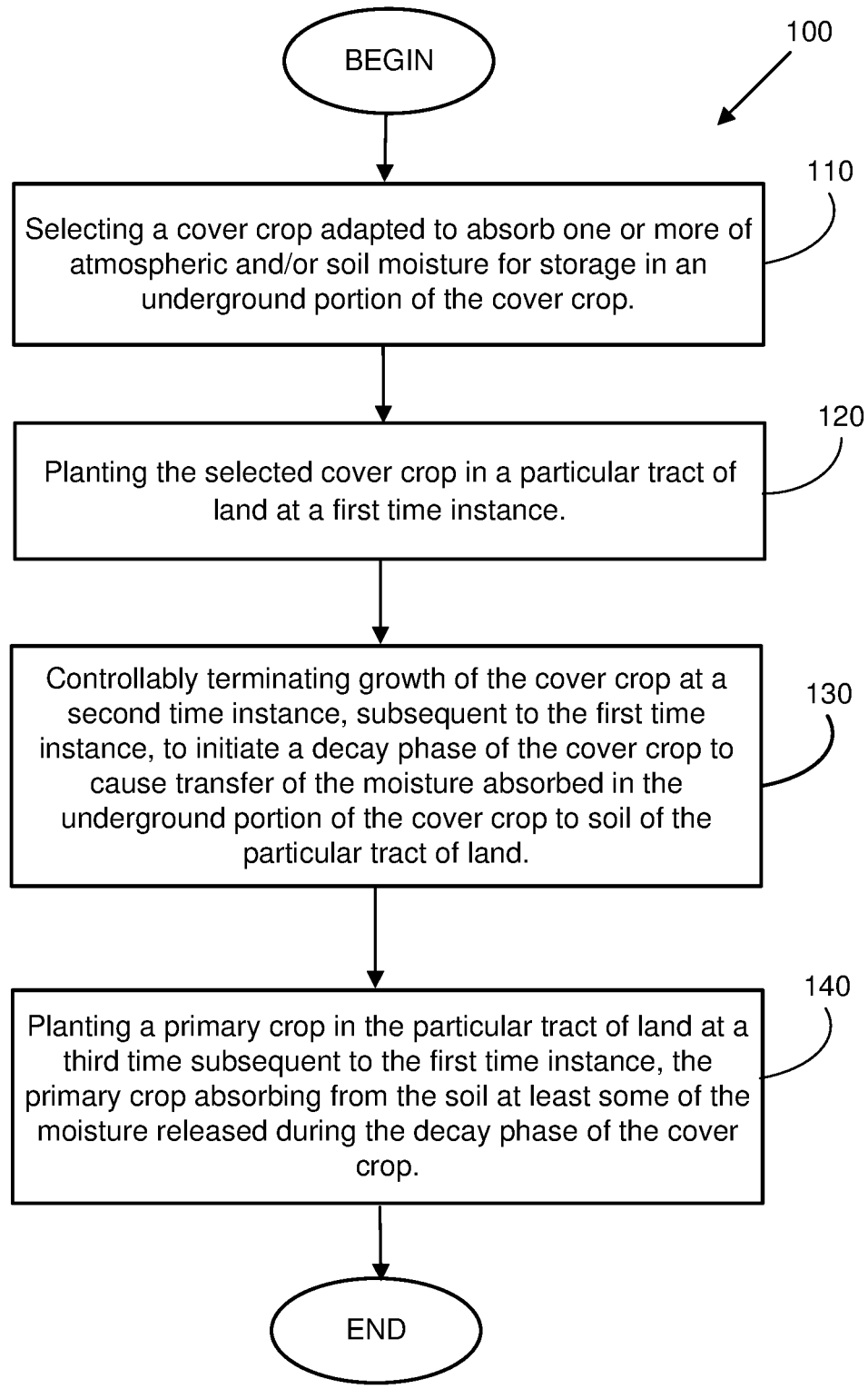

TECHNIQUES AND IMPLEMENTATIONS FOR IMPROVED CROP YIELDS IN ARID CONDITIONS

CROSS-REFERENCE TO RELATED APPLICATIONS

This application claims the benefit of, and priority to, U.S. Provisional Application No. 63/239,440, entitled "TECHNIQUES AND IMPLEMENTATIONS FOR IMPROVED CROP YIELDS IN ARID CONDITIONS," and filed Sep. 1, 2021, the content of which is incorporated herein by reference in its entirety.

BACKGROUND

Under current agricultural practices, certain important crops, such as wheat and different types of grains that absorb a significant portion of water and other nutrients they require from the soil, are planted, in a particular tract of land, at set time intervals in order to let the soil be replenished. For example, wheat grown in the Northwestern part of the United States is generally planted and grown every other year. Due to climate change this planting cycle may need to be pushed back to once every 3 years. The economic consequences of longer wait periods can be significant, not only to individual farmers, but to national as well as global food supply chains.

SUMMARY

In some variations, a method is provided that includes selecting a cover crop adapted to absorb atmospheric moisture for storage in an underground portion of the cover crop, planting the selected cover crop in a particular tract of land at a first time instance, and controllably terminating growth of the cover crop at a second time instance, subsequent to the first time instance, to initiate a decay phase of the cover crop to cause transfer of the moisture absorbed in the underground portion of the cover crop to soil of the particular tract of land. The method further includes planting a primary crop in the particular tract of land at a third time instance, the primary crop absorbing from the soil at least some of the moisture released during the decay phase of the cover crop.

In some variations, a kit is provided that includes cover crop seeds for planting in a particular tract of land at a first time instance, the cover crop seeds producing a cover crop adapted to absorb atmospheric moisture for storage in an underground portion of the cover crop. The kit further includes primary crop seeds for planting in the particular tract of land at a third time instance, the primary crop seeds producing a primary crop adapted to absorb from the soil at least some of the moisture released during a controllable decay phase of the cover crop occurring after a second time instance, subsequent to the first time instance, during which growth of the cover crop is controllably terminated to cause transfer of the moisture absorbed in the underground portion of the cover crop.

Embodiments of the method any of the features described herein. Embodiments of the kit includes any of the features described herein, including any of the features of the method. Other features and advantages of the invention are apparent from the following description, and from the claims.

BRIEF DESCRIPTION OF THE DRAWINGS

These and other aspects will now be described in detail with reference to the following drawings.

FIG. 1 is a flowchart of an example procedure to improve crop yields.

DESCRIPTION

Disclosed are systems, methods, techniques, and other implementations for improved crop yields, for example in arid conditions, or for soils with depleted resources. The idea in the approaches described herein is to use a cover crop to add moisture and other nutrients to the soil to benefit a subsequent primary crop. This is achieved by utilizing a cover crop plant that stores moisture in its root, and transfers, through a process of translocation from the plant's parts (stem, leaves, root, etc.), moisture and nutrients to the root. For instance, a potato, which develops its energy storage portion (tuber) underground, collects moisture (usually from the soil) that it stores in its underground portion. In some embodiments, a cover crop, such as a potato, may be genetically engineered to adapt it to also collect moisture through its leaves, and to transfer that moisture to its underground portion. This collected moisture can then be stored until such time as desired. The cover crop can then be allowed to die (e.g., subjected to a process that terminates its growth) in order to decay and thus release moisture to the cash crop (i.e., the primary crop).

The approaches described herein are advantageous and useful in many situations, including, but not limited to, arid environments. Consider, for example, a situation involving the growing of wheat in the Northwestern part of the United States. Wheat can generally be grown every other year, and due to climate-change that may be pushed back to every 3 years. In these regions of the United States, crop planting is delayed until the soil moisture is high enough to raise a crop on the existing soil moisture. In the approaches and solutions described herein, a cover (sacrificial) crop that can infuse the soil with moisture and nutrients would significantly help agricultural planning and harvests by using cover plants to capture humidity, dew, and any precipitation that would otherwise not reach the soil. Such cover crops also hold moisture that would otherwise be lost to groundwater in an event of high precipitation. Under current agricultural practices, there is considerable waste of precious water and other soil resources.

Some crops are planted so as to be converted to mulch in order to prevent moisture loss. In arid areas this is not feasible because typically such cover crops (e.g., rye) pull out too much moisture from the ground and the pros are outweighed by the cons. In contrast, in the approaches described herein, crop types that add moisture to the soil are selected to act as cover crops. Such selected cover crops may be plants, like potatoes, with a root mass that will act as moisture storage in the ground. Such plants may be adapted (e.g., through genetic engineering techniques) to pull in moisture through the plants' above-surface parts and store it in their root system. The plant may then be killed to cause decay of the plant that will result in release of the stored moisture (and other nutrients) back to the ground through the decaying process. Killing the plant may be performed, for example, by cutting the above-ground foliage of the cover crop (e.g., potato vine for a potato-type cover crop; the mechanical cutting of the foliage may be performed based on a flail mowing and rolling procedure), and/or applying a chemical agent, such as a desiccating agent (e.g., applying glyphosate to potato vines, or applying some other herbicide or chemical agent that is not harmful to the primary crop). The controllable killing of the cover crop will benefit the subsequent primary crop by increasing moisture in the ground which will aid in the growing of the primary crop.

The approaches described herein also include engineering new species of cover crops (through genetic modification/engineering processes) to generate modified species with enhances ability to, for example, absorb moisture and nutrients for storage in the underground fruit portion of the crop, absorb moisture through leaves (for transfer to the root portion of the plant, such as a potato) increase the rate of decay once the cultivation/growth phase of the cover crop is deliberately (and controllably) terminated. Examples of transformation processes to genetically modify cover crops (such as potato) include identifying and isolating genes with desirable traits, and incorporating the identified gene into a vector that is introduced into the target cover crop based on techniques such as agrobacterium-mediated transformations, virus-mediated transformation, etc. To get a consumable GMO crop to market takes considerable research and resources. There are many hurdles and much red tape. On the other hand, getting a cover crop approved will not take as nearly as long because it is not being used as an end product. It is simply a sacrificial secondary supplemental plant.

In some embodiments, the primary and cover crop may be planted at the same time. The primary crop may be one that is adapted (through its natural characteristics, or through engineered genetically modified approaches) to remain dormant until a desired time such that the primary crop will not be affected (or at least have will be minimally affected) by the cover crop consuming soil and moisture resources. Planting the primary and cover crops at substantially the same time could prevent having to overseed during the growing season, and will allow the primary crop to be exposed to more light (and available nutrients that would not have been consumed by the cover crop) than if the primary crop would have been planted at a later point.

The cover crops used may be genetically modified to resist residual chemicals that benefit a primary crop. In some embodiments, the cover crop could be engineered (bred) to finish its life cycle in a way that best benefits the primary crop. For example, the cover crop could be adapted to die off before the primary is planted, and then begin to decay according to a predetermined timeline/profile. A cover crop could be a perennial or annual crop, and could be selected so as to die from frost, or to live through the winter (depending upon differing needs). The cover crop could be designed to die at certain predetermined times regardless of life cycle.

It is to be noted that genetically modified cover crops could be engineered to thrive in a desert/arid environment (e.g., the cover crop may be a genetically modified plant for an environment that has little plant life). Engineered cover crops can be designed to absorb and store carbon, and then seeded in arid regions, not necessarily for the purpose of increasing yield of a primary crop, but also to accrue other environmental benefits. This could dramatically help with climate change since much of the land mass on earth is arid land (i.e., deserts). There is plenty of sunlight energy and carbon in deserts. The problem is lack of moisture, and other desert stressors such as high salt environments. With an appropriately modified cover crop, carbon sequestration may be greatly increased in the world's deserts. This could also benefit landowners of desert land to earn valuable carbon credits. Use of cover crop for such purposes could thus build topsoil in the arid land areas, and better mitigate erosion as well. Genetically modified plants may also be edible to livestock in desert areas. This could provide huge benefits to livestock producers in such environments.

In some examples, a crop rotation can be established whereby the entire growing season is dedicated to growing cover crops for the benefit of the following year(s) primary crop as a way of mitigating wildlife damage. Cover crops could thus be used that are inedible to certain nuisance wildlife (e.g., deer). An example would be a cover crop that benefits a primary crop like corn which is less susceptible to deer damage than, for example, soybeans. Corn is a grass plant, whereas soy is a broadleaf plant. Rotating these vastly different plants may achieve many benefits. For example, a cover crop could be made from a broadleaf plant like a potato, whose leaves are inedible (or genetically modified to be inedible). Under this example approach, one season of growth could be dedicated to help the next year's crop, whilst still being able to get the benefits of a crop rotation, without suffering as much damage from an invasive species. It would be beneficial to get a crop rotation in a place where there is nuisance animal pressure (e.g., such as from deer that eat plants like soybeans), thus avoiding having to grow only one type of crop, such as corn, to stay profitable). Thus, in some of the example approaches described herein, creating a crop rotation system that still delivers similar yield benefits, and still gets the advantages of a rotation, but is not as susceptible to wildlife damage can be achieved. In essence, this gives an entire growing season to a plant that is not susceptible to a certain pest, with different characteristics to a primary for the benefits of a rotation, that stores yield potential for the next year's non-susceptible primaries growing season. In some examples, genetically modified sea plants to sequester carbon may be used.

The approaches and solutions described herein can also greatly help with climate change. Currently, there are a number of carbon-capture programs available to farmers. Farmers get paid valuable carbon credits for putting out cover crops in between primary cash crops. The problem is that the current cover crops used are drying out the soil, which is a problem that is being exacerbated by climate change and resultant lower average precipitation. Under the approaches and solutions described herein, carbon could be sequestered, and moisture can be added to the soil simultaneously. This would incentivize the implementations of cover crop programs, and may also make it a necessity to stay competitive. It would help greatly with the feasibility of using cover crops to fight climate change by sequestering carbon.

In some embodiments, the selected cover crops could be configured (e.g., through genetically modifying processes) to decay at a rate that coincides with the primary plant's needs. Certain cover crops could be tailored to certain environments and to certain primaries to release moisture when such release is needed, thus further eliminating wasted moisture. This would greatly help the primary plant as there are certain times when moisture is much more beneficial to yield. For example, the rainband is usually lower as the warm season progresses, and the implementations described herein could provide a way to extend moisture into the dryer times of the year.

Another feature of the approaches and solutions described herein includes using non-harvested sacrificial cover crops to support the primary crop is the feature of energy transfer. A cover crop is generally run after a primary crop in the "off season." In some situations, the cover crops can be planted before the primary crops are harvested. This generally occurs when the primary crop has finished its life cycle and is drying out to be ready for harvest. In the time between when the cover crop is applied (generally in late summer with corn), and when the next year's crop is to be planted in the spring, there are a lot of growing days with a lot of sunlight that are not being utilized.

More particularly, corn senescence occurs near the end of grain fill (times vary, but in the mid-Atlantic region of the U.S.A. corn senescence typically happens around early August). There is enough sunlight, moisture, growing weather (temperature-wise) under a dying or dead primary crop for a cover crop to grow on the soil beneath the primary crop before the primary crop is harvested. Since the primary plant's life cycle is near the end or has ended, the presence of another species has no effect on yield (the cover and primary crops do not compete for resources at that point). Farmers can take advantage of this situation by applying a cover crop (that can be placed on top of the soil) with a helicopter (or plane, or certain outfitted ground equipment) and a spinner attached beneath with a cable. The cover crop is applied in order to take advantage of the time between senescence, and plant dormancy (which occurs months later in the winter). This strategy provides an opportunity to get a lot of plant growth before the primary crop is harvested (typically in the Fall). This strategy prevents all of the sunlight, moisture, growing weather, etc., to not be wasted after the onset of senescence (which may result in 3-4 months of extra growth time for the cover crop). In the Mid-Atlantic region of the U.S.A., harvesting typically starts in late September, and ends in January. Spreading a cover crop (that can grow without soil incorporation) early can thus give 1-3 months of extra growth for the cover crop. In some examples, farmers may start putting cover crops on while the primary plant is only a foot tall and has a lot of growth left. In this example, the cover crop can then have approximately five (5) months of cover crop growth. Typically, such an early application of a cover crop will not hurt yields of the primary crop, as long as there is adequate moisture (e.g., from irrigation). Accordingly, with adequate moisture, cover crops can be applied long before senescence, thus avoiding waste of much available sunlight and good growing conditions.

Selected cover crops planted in the soil may also be adapted to produce an energy source, e.g., sugar, in order to provide energy and possibly building blocks to next year's crop (e.g., in the form of long chain molecules). This energy would be pulled in through the primary plants root system and translocated to the rest of the plant in order to build and feed the plant. When a corn plant cannibalizes itself due to stressors, it takes carbohydrates from leaves, stems, and roots and prematurely puts this energy into the grain. It also puts out and takes back in carbs through its root, to feed beneficial organisms like micro fungi under normal conditions. Conversely, with the atmospheric moisture-trapping cover crops discussed herein (i.e., crops that pull moisture from the atmosphere for storage underground), carbohydrates are taken from the sacrificial cover plant to feed the primary plant in order to get more energy to the end-result product (i.e., the grain). Grain is simply a fuel that is made through photosynthesis by the building of complex molecules that can then be broken down for energy. The cover crops discussed herein may be used to add to this process by storing energy in the form of a carbohydrates that are made available in the dying root of the cover crop, that the primary can then tap into and move into itself to use as a supplement resource to build itself up faster, and in the end produce more of the grain (or fruit or nuts of the primary crop, as the case may be). Through this approach, a primary crop taps into stored energy from a cover crop. There is much wasted sunlight energy in current farming systems, and with the modifications proposed herein such waste could be greatly mitigated.

In embodiments in which a sugar source is available to a young plant, the plant could break this down for energy/heat which would be beneficial in early spring when the plant is young and it is generally growing in colder conditions than would be optimal. The plants generally have a very stressful time when they are young, and the planting operation usually take place when it is still cold. Breaking down these carbs for heat in order to warm young plants could help getting plants larger and more mature at an accelerated rate, as well as to reduce stresses. This would all benefit the end product.

In some embodiments, a cover crop may be created and tailored to specific primary crops in order to maximize benefits of its macro nutrients as well as micronutrient makeup. For instance, a soybean produces a lot of oils and proteins. Fat and proteins cam thus be translocated to the primary crop. This potential tailored makeup may have an added benefit of conserving resources of changing carbs to oils and proteins (macros). Micronutrients (also referred to as micros), such as vitamins, may be utilized as well.

In some embodiments, the cover crop could be designed so that the energy stored through various forms does not degrade and is made available at specific times that would benefit primary crops. In such embodiments, the cover crop may be adapted to essentially match the needs of the primary crops at differing growth stages.

In some embodiments, the cover crops may be placed at strategic distances from primary crops in order to have better effect on overall system, e.g., plant a cover crop in a row that is five (5) inches away from a row of the primary. In such embodiments, different distances may be more optimal for different primary crops, different environments, and/or different cover crops.

In some embodiments, the primary crops to be planted may themselves be bred or modified in order to better take advantage of the cover crop root benefits. Types of engineered modifications that can be realized for primary crops may include improving the root nutrient uptake of carbs and translocation to other systems in the primary crop. The primary crop may also be adapted to better utilize ground moisture transferred into the soil through the cover crop used. Such a primary crop may also be engineered to possibly excrete a digestive in order to better break down the cover crop root, as well as to have better control of the decay, and/or to be adapted to penetrate into a root.

Cover crops may be used to access fertilizer from the surrounding area in order to be more readily available (e.g., by taking phosphorus from deep in the soil). These systems can also be combined with current cover crop systems, where a plant that is currently used to take nitrogen from the air and store it, can be used as a fertilizer for the primary. Thus, selected cover crops may be used to collect fertilizers materials that are already being consolidated into the cover crop for easy access, and to produce complex molecules through photosynthesis that the primary crops can translocate without having to break them down and rearrange such molecules.

As noted, one of the objectives of the approaches and solutions described herein is to mitigate climate change through carbon sequestration, whilst improving current farming systems in order to increase yield of primary crops by improving current cover crop systems. Implementations of the frameworks and technologies described herein are thought to have the potential to greatly increase profit margins for farmers/growers, such that the implementation of cover crop-base systems will become necessary in order to stay competitive. This could create an incentive to less affluent countries that cannot afford to subsidize with carbon credits to still have high enrollment. In other words, the use of cover crop systems would have multiple economic benefits, each of which could potentially incentivize and spur participation by different stake holders (farmers, corporations and their shareholders, countries throughout the globe) regardless of subsidies, in order to remain competitive.

Current cover crop systems (e.g., that are transformed to mulch, but are not designed for atmospheric moisture capture for soil enrichment) do not always add benefit and in some cases rob benefits. The present approaches and solutions seek to address and remedy some of the major problems with this. In light of climate change and the need to capture carbon, these improvements will be very beneficial to the overall health of the planet. Crops cannot be grown without moisture. If a cover crop depletes moisture, this becomes a problem. The cover crops may also be designed to support the microbiome by feeding it sugar to strengthen it for the primary. Genetic modification could also create a plant that suppresses certain pests in the microbiome. Such crops could also be bred with, for instance, B.T. (*Bacillus thuringiensis*), which is a natural insecticide in order to further suppress pests.

In some examples, selected cover crop (genetically modified or otherwise) can be bred/engineered to be less susceptible to diseases that may occur through the rotting of the cover crop after their growth has been terminated (i.e., after they have been killed). Such cover crops may also be modified to have natural ways to fight infection. The primary crops that are planted may have to be bred to also better fight off root diseases. This would be due to a rotting root from the cover crop becoming an easy host for disease. As noted, cover crops have the potential to bring life to a desert and make non-arable land, arable. Through genetic modification, super cover crops, adapted for capture of atmospheric moisture and infusion into the soil, can be engineered to grow in the desert and capture carbon that otherwise would not happen. In such embodiments, a cover crop can be created that can flourish in a desert environment, and that is engineered to capture and store carbon in the ground.

It is to be noted that the rainband (i.e., expected average precipitation based on historic data charts per time of year) is usually lower on average as the warm growing season progresses. Growers routinely choose crops that are tailored to the rainband, and consequently the growing season is often cut prematurely. However, if a root-based crop that can transfer moisture to the ground was used, this could minimize the effects of the rainband being later in the dryer part of the season through controlled decay of the root, and the release of moisture. This could have profound effects on extending the growing season of many primary crops. This approach to extend the availability of moisture could have the potential to increase the growing season, thus increasing sunlight energy gathering, and thus increasing yield. Essentially it could cause growers to pick different maturity primaries due to more moisture being available later in the season. It would also mitigate risk in most current non-irrigated systems. A grower could also mitigate risk when planting later in the growing season. This could allow for later, generally warmer planting dates. Currently, growers are stuck between putting the crop in cold soil (which has its own inherent risks) to better take advantage of the rainband, or planting later in warmer soil and getting further away from the rainband at critical plant growth stages (such as tasseling).

In some examples, a primary crop could be supplied with a fuel source (such as sugar) for energy. It would likely be used to breakdown this fuel for heat in the typically cold spring season which would limit much stress. It could also use this energy source for any other process such as mechanical energy etc. This would likely be done by breeding primaries to absorb fuels (e.g., carbs) through their roots. This fuel would likely be placed in or close to the root zone at planting. This could prove very beneficial to young plants early in the growing season. This outside energy would most likely supplement the already present solar energy at early growth stages, in order to get a plant established so as to become larger faster, thus making it able to gather inputs more easily.

Thus, with reference to FIG. 1, a flowchart of an example procedure 100 to improve crop yields is shown. The procedure 100 includes selecting 110 a cover crop adapted to absorb one or more atmospheric and/or soil moisture for storage in an underground portion of the cover crop, and planting 120 the selected cover crop in a particular tract of land at a first time instance. In some examples, the selected cover crop may include a potato crop. In some embodiments, selecting the cover crop may include engineering a modified cover crop from an existing cover crop species, with the engineered modified crop including one or more of, for example, enhanced atmospheric moisture capturing characteristics, improved decay phase characteristics, improved energy storage characteristics, and/or enhanced mineral and nutrients capturing characteristics. The engineered modified crop including the improved energy storage characteristics may be adapted to include energy storage behavior that causes moisture to be transferred from a top portion of a root mass of the cover crop to a lower portion of the root mass. In some examples, the engineered modified crop including the improved energy storage characteristics may be adapted to include energy storage behavior that causes moisture to be transferred from above-ground leaves of the cover crop to a buried root mass of the cover crop. The improved decay phase characteristics may include decay behavior that causes a root mass of the cover crop to decay into humic acid. The enhanced mineral and nutrients capturing characteristics may include capture behavior to capture potassium from rocky materials. In some embodiments, the engineered modified crop may be configured to decay according to a predetermined decay profile that releases nutrients and energy molecules stored in the cover crop according to a predetermined gradual timeline, with the released nutrients and energy molecules being absorbed by the primary crop.

With continued reference to FIG. 1, the procedure 100 further includes controllably terminating growth of the cover crop at a second time instance, subsequent to the first time instance, to initiate a decay phase of the cover crop to cause transfer of the moisture absorbed in the underground portion of the cover crop to soil of the particular tract of land. Controllably terminating growth of the cover crop may include causing biological destruction of above-ground foliage absorbing the atmospheric moisture. In some embodiments, causing the biological destruction of the above-ground foliage may include one or more of, for example, mechanically cutting the above-ground foliage, and/or exposing the above-ground foliage to a desiccating chemical agent.

As further shown in FIG. 1, the procedure 100 additionally includes planting 140 a primary crop in the particular tract of land at a third time, the primary crop absorbing from the soil at least some of the moisture released during the decay phase of the cover crop. In some examples, planting the primary crop is performed prior to the second time instance at which controllably terminating growth of the cover crop is commenced. In some examples, planting of the primary crop at the third time instance may include one of planting the primary crop at the third time instance subsequent to the first time instance, or planting the primary crop at the third time instance occurring before or substantially proximate to the first time instance.

In some example embodiments, planting the primary crop may include selecting an engineered modified primary crop, from an existing primary crop species, with the engineered modified primary crop including one or more of, for example, sugar absorption characteristics to absorb sugar molecules from the cover crop during the decay phase of the cover crop, improved energy storage characteristics, and/or improved moisture capture and storage characteristics adapted to absorb and retain moisture from above-ground leaves of the primary crop.

The implementations described herein also include a kit comprising cover crop seeds for planting in a particular tract of land at a first time instance, the cover crop seeds producing a cover crop adapted to absorb atmospheric and/or soil moisture for storage in an underground portion of the cover crop. The kit further includes primary crop seeds for planting in the particular tract of land at a third time instance, the primary crop seeds producing a primary crop adapted to absorb from the soil at least some of the moisture released during a controllable decay phase of the cover crop occurring after a second time instance, subsequent to the first time instance, during which growth of the cover crop is controllably terminated to cause transfer of the moisture absorbed in the underground portion of the cover crop.

Additional Embodiments

Further details about additional embodiments of the approaches, solutions, and implementations described herein are follow below.

The proposed approaches and implementations include a plant that has been modified to have the ability to parasitically harvest sugars from a secondary crops roots in order to take sugars from roots of secondary for sugar supplementation of a primary. Such sugars will then be translocated to the most beneficial areas of a primary in order to have the most benefit for plant growth. This would have the benefit of giving a primary plant an aid in plant growth and providing sugars that the plant would not have to create. The plant uses sugars that are made in its leaves to provide energy for growth. This would provide energy that the plant could use as a substitute to aid in primary crop development and growth.

Some embodiments include a plant that has been modified to transfer moisture lower into its root mass from a location higher in its root mass. A few plants have the ability to transfer moisture within the root mass itself. Normally a plant will transfer moisture up to the exposed parts of the plant, e.g., stems leaves, etc. Certain plants have adapted the ability to transfer moisture deeper within a root mass in order to store moisture from a light rain event that only reaches the exposed layer of the soil. This ability could be very useful in the creation of a secondary crop that is designed to harvest moisture for storage. Basically, moisture from light rains that would normally not penetrate into the lower soil levels (and would thus normally be evaporated by heat and sunlight) could be harvested and stored deeper for a primaries use at a later date. The deeper the stored moisture, the less risk there is for environmental loss of the moisture through evaporation. Thus, a root mass or tuber that has smaller surface roots which pull moisture into lower deeper root levels for storage is configured to store moisture under such conditions.

The approaches described herein include a method of inoculating a cover crop for the root to better rot into humic acid. Humic acid is the substance that is degraded plant material that turns into topsoil. Humic acid is primarily made up of carbon. By inoculating a plant for its root to more readily, and at a higher ratio, be converted to humic acid, the ability to increase topsoil, as well as pull carbon from the air, is improved. Topsoil soil has many advantages for crop growth and is generally very desirable. There are various micro-organisms that have this ability that could be used for this purpose.

Example embodiments include a plant (such as potato, or any other plant that can serve as a cover crop) that has been modified to pull moisture from the air through its leaves, and to send the moisture down to its roots. In some examples, primary crop may also be similarly modified to adapt to this behavior of absorbing and retaining moisture from the atmosphere. There are a few plants that have been recently discovered to have this ability. Some plants can pull moisture from their roots and then translocate the moisture up through their stems and into their leaves. Recent discoveries have identified plants (located in cloud forests) which have adapted the ability to pull moisture through their leaves and translocate said moisture down to their roots. Such plants can not only send moisture down to their roots, but also have the ability to push it out of their roots in order to moisten the ground in order to germinate their seedlings. This could prove very useful in a supplemental/cover crop system. It would have several advantages. One would be that of pulling moisture out of the air for plant growth as well as for moisture storage. Much of the moisture in the atmosphere that could aid in plant growth is lost because only a small number of plants have these moisture absorbing characteristics. The secondary crop could also have the ability to drop the humidity within a primary crop canopy. This could prove useful for drying a crop like corn or soybeans. The crop should be dry in order for it to be harvested, and many times shorter maturity length varieties are planted so that there is ample summer heat to dry them. In some embodiments, a plant could be developed to pull this moisture away from the crop faster and store it, resulting in longer maturity/higher yielding crops using less energy to dry crops. This would also have the advantage of utilizing moisture that would otherwise not be used and storing it for the next crops use which could prove very useful in arid environments.

The approaches include primary plants that have been modified to have the ability to transfer macro and micro-nutrients from a secondary supplemental plant. The ability to grow a supplemental plant in between primary crop growing seasons would have several advantages. Rather than just parasitically drawing sugars from a secondary to a primary, the ability for a primary to take some or all of the long chain molecules that would benefit it could also be developed. It takes time and energy to create the various molecules that a plant needs to grow. By having a readily available supplemental source, a primary crop is greatly aided in its growth in order to produce higher yields. As a result, a secondary crop, like a radish, could be developed that would have a similar molecular profile for the following years corn plant to provide it with the nutrition it would require at about the same time it would require to maximize yield. In other words, the approaches described herein include creating primary and secondary crops for the purpose of the primary crop feeding off of the secondary. These crops would act in unison (in cooperation) to create a piggyback effect so as to take advantage of times between growing seasons in order to produce a higher crop yield.

In some embodiments, a secondary crop may be designed to harvest specific nutrients from a soil. In many areas there are soils that are high in nutrients like potassium, but which are in an unavailable form for plant growth. An example would be much of the farmland in south eastern South Dakota. In this particular region it has been estimated that they have enough potassium for 200 years of crop growth. The problem is that the potassium is available in large stones and is generally unavailable for crops. However, a secondary crop could be designed to dissolve and harvest specific nutrients like potassium, leaving them in a state readily available for a primary crop to absorb once the secondary crop has decayed. An example would be a secondary crop that was developed to have a root that has an advanced ability to harvest potassium. Such a root will also call for a high level of potassium in order to increase potassium storage. Likely an inoculant bred for this purpose will have to pair with said root in order to net the highest yields. This would greatly reduce the need for mined fertilizers throughout the world, and greatly help a farmer's profit margin. This technique could be used for any other desired, but otherwise inaccessible (or unavailable in a convenient extractable form) nutrient.

As noted, the approaches described herein include the idea of using a cover crop to add moisture to the soil to benefit a primary crop. This can be done by utilizing a cover crop plant that stores moisture in its root. In some examples, this solution can be achieved through genetically modifying various cover crops (such as potato) so that they are adapted/configured to achieve a process of translocation from all of the plant's parts (stem, leaves, root, etc.) to the root. For instance, a genetically modified potato may be engineered to have its fruit under the ground, take moisture pulled in through its leaves and store it in the root mass in the ground. This moisture can then be stored until such time as desired. The cover crop (be it a potato, whether adapted according to one or more of the above described characteristics) can then be killed (controllably terminated) in order to decay and thus release moisture to the cash crop aka primary. There are many systems which this will be useful, including, but not limited to arid environments, i.e., wheat in the NW United States. Wheat generally can be grown every other year, and due to climate change that may be pushed back to every 3 years. These areas wait until the soil moisture is high enough to raise a crop on the provided soil moisture. The proposed solutions would significantly help by using the plant to capture humidity, dew, and any precipitation that would otherwise not reach the soil to be stored. It would also hold moisture that would otherwise be lost to groundwater in an event of high precipitation. In the current system there is much waste of precious water. Also, cover crops are currently used to provide mulch. This is to aid in moisture loss. In certain arid systems this is not feasible. The cover crop (rye) pulls out too much moisture from the soil and the pros are outweighed by the cons.

The solutions proposed herein implement a cover crop system which adds moisture to the soil by utilizing a plant with a root mass that will act as moisture storage in the ground. This plant will pull in moisture through all plant surfaces and store it in its root system. Said plant will then be killed (e.g., controllably killed) so that it starts decaying in order to release stored moisture back to the ground through the decaying process. This will benefit the following primary crop by increasing moisture in the ground which will aid in the growing of the primary.

The proposed solutions include genetically modifying existing plants in order to rapidly achieve the objective and goals described herein. In order to get a consumable GMO crop to market takes considerable research and resources. There are many hurdles and much red tape. Getting a cover crop approved will not take nearly as long because it is not being used as an end product. It is simply a sacrificial secondary supplemental plant.

The proposed solution and approaches system will greatly help with climate change. Currently there are many carbon capture programs for farmers. Farmers/producers get paid valuable carbon credits for putting out cover crops in between primary cash crops. The problem is that the current cover crops used are drying out the soil which is being exasperated by climate change and subsequently lower average precipitation. Under the purposed approach carbon could be sequestered and add moisture to the soil simultaneously. This would make the implementation and adoption of such cover crops much more rapid as well as a necessity to stay competitive. It would help greatly with the feasibility of using cover crops to fight climate change by sequestering carbon.

Cover crops could be created and adapted to decay at a rate that coincides with the primary plant's needs. Certain cover crops could be tailored to certain environments and to certain primaries to release moisture when it is needed, thus further eliminating wasted moisture. This would greatly help the primary plant as there are certain times when moisture is much more beneficial to yield. The rainband is usually lower as the warm season progresses, and this could be a way to extend moisture into the dryer times of the year.

A second aspect of using non harvested sacrificial cover crops to support the primary crop is that of energy transfer. A cover crop is generally run after a primary crop in the "off season". Sometimes they are flown on with helicopters before the crop is even harvested. This is generally when the primary has finished its life cycle and is drying out to be ready for harvest. In the time between when the cover crop is applied generally in late summer with corn, and when the next year's crop is to be planted in the spring, there is a lot of growing days with a lot of sunlight that are not being utilized. The proposed approaches include using a cover crop to produce an energy source, most likely sugar, in order to provide energy and possibly building blocks to the next year's crop (long chain molecules). This energy would be pulled in through the primary plants root system and translocated to the rest of the plant in order to build and feed the plant. When a corn plant cannibalizes itself due to stressors it takes carbohydrates from leaves, stems, and roots and prematurely puts this energy into the grain. It also puts out and takes back in carbs through its root to feed beneficial organisms like micro fungi under normal conditions. Embodiments of the proposed approaches "hijack" this system in order to take carbohydrates from another sacrificial plant and feed the primary plant in order to get more energy to the end result, i.e., grain. Grain is simply a fuel that is made through photosynthesis by the building of a complex molecule that can then be broken down for energy. The proposed approaches can be adapted to use a cover crop in order to add to this process by storing energy in the form of a carbohydrate in an available form such as a dead root that the primary can then tap into and move into itself to use as a supplement to build itself up faster and in the end produce more grain (or fruit, nuts, or any other crop whatsoever).

The proposed approaches find a way to have a primary tap into stored energy from a cover crop. There is much wasted sunlight energy in existing current farming systems, which the modifications proposed herein could greatly mitigate. For example, if there is a sugar source available to a young plant it could break this down for heat which would be beneficial in early spring when the plant is young, and it is generally in colder than optimal conditions. The plants generally have a very stressful time when they are young and the planting time usually takes place during cold weather. There may be a way to break down these carbs for heat in order to warm the young plant. This would greatly help with getting plants established, larger, and more mature at an accelerated rate, as well as reduce stress experienced by such plants. This would all benefit the end product.

In some embodiments, cover crops may be created and tailored to specific primary crops in order to maximize benefits of its macro nutrient as well as micronutrient makeup. For instance, a soybean produces a lot of oils and proteins. There may be a way to translocate a fat and proteins to the primary crop. This potential tailored makeup may have an added benefit of conserving resources of changing carbs to oils and proteins (macros). This change takes effort and energy and that is something to mitigate. The micros such as vitamins may be utilized as well.

Cover crops could be designed so that the energy stored through various forms does not degrade and is made available at specific times that would benefit primaries, by essentially matching the cover crop to the needs of the primary at differing growth stages. Cover crops may be placed at strategic distances from primary crop in order to have better effect on the overall system, e.g., placing individual cover crop seeds/plants in a row 5 inches away from a row of the primary crop. Possibly, different distances for differing primaries and differing environments may be used for specific planting configurations.

In some embodiments, primary crops may be bred or modified in order to better take advantage of the cover crop root benefits. Examples changes to the characteristics of such crops may include changes that improve the root nutrient uptake of carbs and translocation to other systems in the primary. Modification to the primary crop may also include changes to adapt the primary crop to better utilizing moisture from the cover crop roots, changes to cause excretions of digesting compounds in order to better break down the cover crop root, changes to better control decay of the cover crop, and/or changes to cause the primary crop to penetrate into a root of the cover crop. Such changes would all potentially benefit yield and consumption of the primary crop.

In some embodiments, cover crops are currently used to access fertilizer from the surrounding area in order to be more readily available (e.g., by absorbing phosphorus from deep in the soil). These systems can also be combined with current cover crop systems, where a plant is currently used to take nitrogen from the air and store it so that it is effectively used as a fertilizer for the primary. The proposed approaches use such these basic fertilizers (atoms) that are already being consolidated into the cover crop for easy access, and making a complex molecule through photosynthesis, which the primary can then translocate without having to break it down and rearrange it.

One goal of the approaches described herein is to help mitigate climate change through carbon sequestration, whilst improving current farming systems in order to increase yield of primary crops by improving current cover crop systems. An objective to achieve with the approaches described herein is to make the technology so profitable to a farmer that the implementations of the proposed cover crop systems will become necessary in order to stay competitive. This will ensure that less affluent countries that cannot afford to subsidize with carbon credits will still have high enrollment. The cover crop systems would, under such circumstances, be so beneficial that they have to be used, regardless of subsidies, in order for farmers to stay financially competitive.

Current cover crop systems do not always add benefit and in some cases reduce benefits. The approaches described herein seek to address and solve some of the major problems that the current system present. In light of climate change and the need to capture carbon, these improvements will be very beneficial to the overall health of the planet. Because you cannot grow crops without moisture, if a cover crop is depleting moisture in most environments, it will become a problem.

The cover crops may also be designed to support the microbiome by feeding it sugar to strengthen it for the primary. Genetic modification could also create a plant that suppresses certain pests in and to the microbiome. They could also be bred with for instance B.T. which is a natural insecticide in order to further suppress differing pests. Crops can also be bred to be less susceptible to diseases that may occur through the rotting of the cover crop after it has been killed. They also could be modified to have natural ways to fight infection. The primary may have to be bred to better fight off root diseases as well. This would be due to a rotting root from the cover crop becoming an easy host for disease.

Cover crops have the potential to bring life to the desert and make non-arable land arable. Through genetic modification, improved ("super") cover crops can be created which will grow in the desert and capture carbon that otherwise would not happen due to the sparsity of living organisms in such environments. Many plants currently survive and have adapted to low humidity environments through various means. The proposed approaches may be configured to adopt some of those adaptation means to create plants to meet the goals discussed herein, creating a cover crop that can flourish in a desert environment that has been bred to capture and store carbon in the ground.

In some embodiments, primary and cover crops can be planted at the same time. For example, GMO cover crops will lay dormant until a desired time such that a primary crop will not be adversely affected (or will only be minimally affected) by the cover crop. This would prevent having to overseed during the growing season, and will allow the growing crops to gather more light to cause them to become more established. These cover crops could be genetically modified to resist residual chemicals that benefit a primary. The cover crops can also be bred to finish their life cycles to coincide with the delivery of the most benefits to a primary. For example, the cover crops can be configured to die off before the primary is planted, and then begin to rot at a pace commensurate with the development/growth of the primary crop. Cover crops could be perennial or annual crop, and could be designed to die from frost or live through the winter, depending upon differing needs. It could also be designed to die at certain predetermined times regardless of life cycle.

Some GMO crops that will thrive in a desert environment may be used. Plants can be genetically modified for an environment that has little plant life. Such plants can be designed to absorb and store carbon, and then seed the deserts of the world. This could dramatically help with climate change since much of the land on earth is desert. There is plenty of sunlight energy and carbon in deserts, but the problem (that inhibits farming) is the lack of moisture and the existence of various desert stressors such as high salt environments. With the right genes in the right plants, carbon sequestration in the deserts of the world can be greatly increased. This could also benefit landowners of desert land to get paid valuable carbon credits. If done correctly, the proposed approaches could build topsoil in the desert, and better mitigate erosion as well.

In some embodiments, genetically modify plants that are edible by livestock in a desert environment may be designed and used. This would deliver huge benefits to livestock producers in such environments.

In some embodiments, a crop rotation could be created where the entire growing season is given to a cover crop for the benefit of the next year's primary to mitigate wildlife damage. You would use a cover crop that would be inedible to problem (pest or nuisance) animals like deer. An example would be a cover crop that would benefit a primary crop like corn which is less susceptible to deer damage than, for example, soybeans. Corn is a grass plant; soy is a broadleaf plant. Farmers often rotate these vastly different plants for many benefits. A cover crop could be engineered (through genetic modification/engineering) from a broadleaf plant like a potato, whose leaves are inedible, or modify one to be inedible. This type of system would give you one season of growth to help the next year's crop, whilst still being able to get the benefits of a crop rotation, without suffering as much damage from an invasive species. It would be very beneficial to get a crop rotation in a place where there is negative animal pressure, e.g., deer that eat plants like soybeans, where farmers are forced to only grow corn to stay profitable, creating a crop rotation system that still delivers similar yield benefits, and still gets the advantages of a rotation, but is not as susceptible to wildlife damage. As a result, such a rotation gives an entire growing season to a non-susceptible plant to a certain pest, with different characteristics to a primary for the benefits of a rotation, that stores yield potential for the next year's non susceptible primaries growing season.

Additional example embodiments include the use of genetically modified sea plants to sequester carbon. While this could be a waste of valuable topsoil producing carbon, it may nevertheless be necessary in light of the current state of the things.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A method comprising:
   selecting a cover crop adapted to absorb one or more of atmospheric or soil moisture for storage in an underground portion of the cover crop;
   planting the selected cover crop in a particular tract of land at a first time instance;
   controllably terminating growth of the cover crop at a second time instance, subsequent to the first time instance, to initiate a decay phase of the cover crop to cause transfer of the moisture absorbed in the underground portion of the cover crop to soil of the particular tract of land; and
   planting a primary crop in the particular tract of land at a third time instance, the primary crop absorbing from the soil at least some of the moisture released during the decay phase of the cover crop;
   wherein selecting the cover crop comprises selecting a modified cover crop engineered from an existing cover crop species, with the engineered modified cover crop including one or more of:
      improved energy storage characteristics including energy storage behavior that causes moisture to be transferred from one or more of: a top portion of a root mass of the cover crop to a lower portion of the root mass, or above-ground leaves of the cover crop to the root mass of the cover crop,
      improved decay phase characteristics that include decay behavior that causes the root mass of the cover crop to decay into humic acid, or
      enhanced mineral and nutrients capturing characteristics that include capture behavior to capture potassium from rocky materials.

2. The method of claim 1, wherein the engineered modified cover crop is configured to decay according to a predetermined decay profile that releases nutrients and energy molecules stored in the cover crop according to a predetermined gradual timeline, wherein the released nutrients and energy molecules are absorbed by the primary crop.

3. The method of claim 1, wherein the selected cover crop includes a potato.

4. The method of claim 1, wherein planting the primary crop is performed prior to the second time instance at which controllably terminating growth of the cover crop is commenced.

5. The method of claim 1, wherein controllably terminating growth of the cover crop comprises:
   causing biological destruction of above-ground foliage absorbing the atmospheric moisture.

6. The method of claim 5, wherein causing the biological destruction of the above-ground foliage comprises one or more of: mechanically cutting the above-ground foliage, or exposing the above-ground foliage to a desiccating chemical agent.

7. The method of claim 1, wherein planting of the primary crop at the third time instance comprises one of:
   planting the primary crop at the third time instance subsequent to the first time instance, or planting the primary crop at the third time instance occurring before or substantially proximate to the first time instance.

8. The method of claim 1, wherein planting the primary crop comprises:
   selecting an engineered modified primary crop, from an existing primary crop species, with the engineered modified primary crop including one or more of: sugar absorption characteristics to absorb sugar molecules from the cover crop during the decay phase of the cover crop, improved energy storage characteristics, or improved moisture capture and storage characteristics adapted to absorb and retain moisture from aboveground leaves of the primary crop.

9. A kit comprising:
   cover crop seeds for planting in a particular tract of land at a first time instance, the cover crop seeds producing a cover crop adapted to absorb atmospheric and/or soil moisture for storage in an underground portion of the cover crop, wherein the cover crop seeds are modified cover crop seeds engineered from existing one or more seeds of a cover crop species, with the modified cover crop seeds including one or more characteristics from:
   improved energy storage characteristics including energy storage behavior that causes moisture to be transferred from one or more of: a top portion of a root mass of the cover crop to a lower portion of the root mass, or above-ground leaves of the cover crop to the root mass of the cover crop,
   improved decay phase characteristics that include decay behavior that causes the root mass of the cover crop to decay into humic acid, or
   enhanced mineral and nutrients capturing characteristics that include capture behavior to capture potassium from rocky materials; and
   primary crop seeds for planting in the particular tract of land at a third time instance, the primary crop seeds producing a primary crop adapted to absorb from the soil at least some of the moisture released during a controllable decay phase of the cover crop occurring after a second time instance, subsequent to the first time instance, during which growth of the cover crop is controllably terminated to cause transfer of the moisture absorbed in the underground portion of the cover crop.

* * * * *